US012127733B2

(12) United States Patent
Taniguchi

(10) Patent No.: US 12,127,733 B2
(45) Date of Patent: Oct. 29, 2024

(54) MOUNT MEMBER AND ENDOSCOPE DEVICE

(71) Applicant: Sony Olympus Medical Solutions Inc., Tokyo (JP)

(72) Inventor: Takuya Taniguchi, Tokyo (JP)

(73) Assignee: Sony Olympus Medical Solutions Inc., Tokyo (JP)

( * ) Notice: Subject to any disclaimer, the term of this patent is extended or adjusted under 35 U.S.C. 154(b) by 533 days.

(21) Appl. No.: 17/437,419

(22) PCT Filed: Feb. 10, 2020

(86) PCT No.: PCT/JP2020/005186
§ 371 (c)(1),
(2) Date: Sep. 9, 2021

(87) PCT Pub. No.: WO2020/195256
PCT Pub. Date: Oct. 1, 2020

(65) Prior Publication Data
US 2022/0151476 A1    May 19, 2022

(30) Foreign Application Priority Data

Mar. 25, 2019  (JP) ................. 2019-055862

(51) Int. Cl.
*A61B 1/12*    (2006.01)
*A61B 1/00*    (2006.01)
*A61B 1/04*    (2006.01)

(52) U.S. Cl.
CPC .......... *A61B 1/121* (2013.01); *A61B 1/00105* (2013.01); *A61B 1/00128* (2013.01);
(Continued)

(58) Field of Classification Search
CPC ............ A61B 1/00066; A61B 1/00105; A61B 1/00112; A61B 1/00128; A61B 1/04; A61B 1/042
See application file for complete search history.

(56) References Cited

U.S. PATENT DOCUMENTS 4,552,131 A * 11/1985 Omagari ............ G02B 23/2453
                                                    600/165
5,792,045 A *  8/1998 Adair ................. A61B 1/00128
                                                    600/125
(Continued)

FOREIGN PATENT DOCUMENTS

JP    H01211716 A    8/1989
JP    H0786590 B2    9/1995
(Continued)

OTHER PUBLICATIONS

International Search Report and Written Opinion mailed on Apr. 7, 2020, received for PCT Application PCT/ JP2020/005186, Filed on Feb. 10, 2020, 8 pages including English Translation.

*Primary Examiner* — Aaron B Fairchild
(74) *Attorney, Agent, or Firm* — XSENSUS LLP

(57) ABSTRACT

Provided are a mount member and an endoscope device by which length of cleaning time can be shortened. A mount member 9 includes a first member 91; a second member 92; and a restriction member 93 that restricts the second member 92 from moving in the direction of a first axis L1, by clamping the second member 92 in a manner allowing rotation, through the first member 91, and that has at least one first cutout cut out such as to expose, to the exterior, a part of a contact section 9211 of the second member 92 clamped through the first member 91.

20 Claims, 18 Drawing Sheets

(52) U.S. Cl.
CPC ............ *A61B 1/00147* (2013.01); *A61B 1/04* (2013.01); *A61B 1/042* (2013.01)

(56) References Cited

U.S. PATENT DOCUMENTS

| | | | | |
|---|---|---|---|---|
| 5,868,665 | A * | 2/1999 | Biggs | A61B 1/00128 600/161 |
| 6,004,263 | A * | 12/1999 | Nakaichi | A61B 1/0607 600/179 |
| 7,387,605 | B2 | 6/2008 | Frith | |
| 2006/0229495 | A1 * | 10/2006 | Frith | A61B 1/00128 600/112 |
| 2016/0128550 | A1 * | 5/2016 | Laser | A61B 1/042 600/109 |
| 2019/0167374 | A1 * | 6/2019 | Calavrezos | A61B 1/0014 |
| 2020/0205646 | A1 * | 7/2020 | Tanahashi | A61B 1/00195 |

FOREIGN PATENT DOCUMENTS

| | | |
|---|---|---|
| JP | 10-234660 A | 9/1998 |
| JP | 2000-227559 A | 8/2000 |
| JP | 2006-223477 A | 8/2006 |
| WO | 2019/026385 A1 | 2/2019 |

\* cited by examiner

MOUNT MEMBER AND ENDOSCOPE DEVICE

CROSS-REFERENCE TO RELATED APPLICATIONS

The present application is based on PCT filing PCT/JP2020/005186, filed Feb. 10, 2020, which claims priority to JP 2019-055862, filed Mar. 25, 2019, the entire contents of each are incorporated herein by reference.

TECHNICAL FIELD

The present disclosure relates to a mount member used for an endoscope and an endoscope device.

BACKGROUND ART

In the medical field and the industrial field, an endoscope device for observing the inside of a test object such as a human being or a mechanical structure has been known (see, for example, PTL 1). The endoscope device described in PTL 1 includes an endoscope (optical tube) for taking in a subject image of the inside of the test object and emitting the subject image; and an endoscope camera head (TV camera) for holding the endoscope and imaging the subject image emitted from the endoscope, and the endoscope is held in a manner of being rotatable around an optical axis set inside relative to the endoscope camera head. In addition, the endoscope camera head includes a mount member and a camera head main body. The mount member has a bottomed cylindrical shape to which an eyepiece section of the endoscope can be fitted. Besides, a bottom part of the mount member is formed with a through-hole penetrating from the face to the back and having a circular shape in plan view. The camera head main body includes a casing and an imaging section which is accommodated in the casing and which images the subject image emitted from the endoscope. Here, an outer surface of the casing is formed with a recess extending in an annular shape with a first axis as a center. Further, the mount member (endoscope) has an edge part of the through-hole of the mount member fitted to the recess of the casing, and, with an outer surface of the edge part (hereinafter referred to as a "casing-side rotational sliding surface") slid on an inner surface of the recess (hereinafter referred to as a "mount member side rotational sliding surface"), the mount member is rotated relative to the camera head main body with the first axis as a center.

CITATION LIST

Patent Literature

[PTL 1]
 JP 2000-227559A

SUMMARY

Technical Problem

However, in the abovementioned PTL 1, the mount member side rotational sliding surface is hidden behind the casing-side rotational sliding surface and is not exposed to the exterior; thus, when cleaning the endoscope camera head, it is difficult to clean between the mount member side rotational sliding surface and the casing-side rotational sliding surface with a cleaning brush, posing a problem that a lot of time is taken for the cleaning.

The present disclosure has been made in consideration of the foregoing, and it is an object of the present disclosure to provide a mount member and an endoscope device by which the length of cleaning time can be shortened.

Solution to Problem

To solve the abovementioned problem and to achieve the above object, the mount member according to the present disclosure includes a first member provided in a camera head having an imaging section; a second member that is rotatable around a first axis passing through the first member and to which an endoscope is connectable; and a restriction member that restricts the second member from moving in the first axis direction, by clamping the second member in a manner allowing rotation, through the first member, and that has at least one first cutout cut out such as to expose, to the exterior, a part of a contact section of the second member clamped through the first member.

In addition, the mount member according to the present disclosure is characterized in that, in the above disclosure, the contact section is formed with a through-hole in which the first member is to be inserted, is rotatable in a state in which the first member is inserted in the through-hole, and has at least one second cutout cut out toward an outer edge side of the contact section from an outer circumferential side of the through-hole.

Besides, the mount member according to the present disclosure is characterized in that, in the above disclosure, the first cutout and the second cutout are formed such that an end part of the first cutout and an end part of the second cutout intersect each other in a case where the end part of the first cutout and the end part of the second cutout overlap with each other.

In addition, the mount member according to the present disclosure is characterized in that, in the above disclosure, the first cutout and the second cutout are formed such that at least one of the end part of the first cutout and the end part of the second cutout is in a tapered shape inclined toward a rotating direction from the end face.

Besides, the mount member according to the present disclosure is characterized in that, in the above disclosure, the mount member includes a spacing-apart section that spaces apart the first member and the second member, the first member has a first rotational sliding surface that clamps the contact section through the second member, and the spacing-apart section is provided at either one of the first rotational sliding surface and a surface on the first rotational sliding surface side of the contact section.

In addition, the mount member according to the present disclosure is characterized in that, in the above disclosure, the second member has at least one slot that extends in the shape of an arc of a circle with the first axis as a center.

Besides, an endoscope device according to the present disclosure includes the mount member according to the above disclosure; and an endoscope that takes in an image of a subject and emits the image, and the second member includes a pressing section that presses the endoscope toward the first axis when the endoscope is connected to the second member.

Advantageous Effect of Invention

According to the present disclosure, an advantageous effect that the length of cleaning time can be shortened is produced.

DESCRIPTION OF EMBODIMENTS

Figure 1:
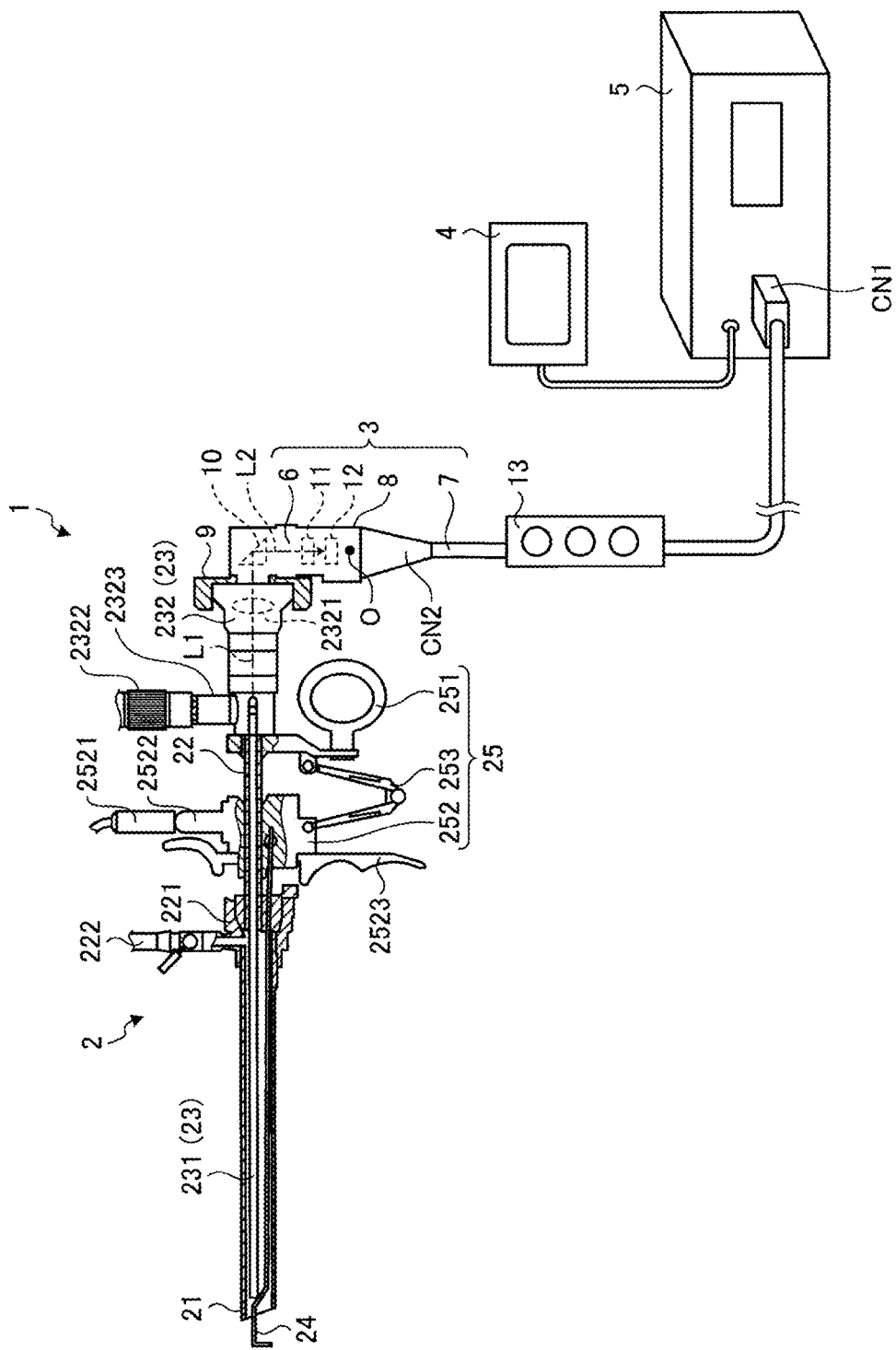
FIG. 1 is a diagram depicting a general configuration of an endoscope device according to one embodiment.

Modes for carrying out the present disclosure (hereinafter referred to as "embodiments") will be described in detail below referring to the drawings. Note that the following embodiment is not limitative of the present disclosure. In addition, each drawing referred to in the following description merely schematically depicts the shapes, sizes, and positional relations to such an extent that the contents of the present disclosure can be understood. In other words, the present disclosure is not limited only to the shapes, sizes, and positional relations exemplified in each drawing. Further, in the description of the drawings, the same parts are denoted by the same reference signs and described. In addition, in the description of the drawings, the same parts are denoted by the same reference signs and described.

[General Configuration of Endoscope Device]

FIG. 1 is a diagram depicting a general configuration of an endoscope device according to one embodiment.

An endoscope device 1 depicted in FIG. 1 is a device which is used in the medical field and for performing a treatment (for example, incisure or the like) of a biomedical tissue while observing the inside of a living body. As illustrated in FIG. 1, the endoscope device 1 includes a resectoscope 2, an endoscope imaging device 3, a display device 4, and a controller 5.

[Configuration of Resectoscope]

The resectoscope 2 is inserted into a living body, and can take in an image of a subject and perform a treatment of a biomedical tissue. As depicted in FIG. 1, the resectoscope 2 includes a sheath 21, a guide tube 22, an endoscope 23, a resection electrode member 24, and a handle section 25.

The sheath 21 is a part which has a cylindrical shape and is inserted into a living body. The guide tube 22 has an outside diameter smaller than an inside diameter of the sheath 21, and is inserted in and passed through the sheath 21. The guide tube 22 has a tip side (the left side in FIG. 1) thereof fixed to the sheath 21 through an attaching member 221 (FIG. 1). Here, the attaching member 221 is provided with a water feed port 222 through which liquid is poured into the sheath 21 and the liquid is sent from the tip of the sheath 21.

The endoscope 23 is a part that takes in an image of a subject, and includes an insertion section 231 and an eyepiece section 232, as depicted in FIG. 1.

The insertion section 231 is fixed in the guide tube 22, and is inserted in and passed through the sheath 21. An optical system that includes one or a plurality of lenses and concentrates an image of a subject is provided in the insertion section 231.

The eyepiece section 232 is connected to a base end (the right end portion in FIG. 1) of the insertion section 231. An eyepiece optical system 2321 by which the subject image concentrated by the optical system in the insertion section 231 is emitted from the eyepiece section 232 to the exterior is provided in the eyepiece section 232. The eyepiece section 232 is formed in a tapered shape with a diameter increased in going toward the right side, and the endoscope imaging device 3 is detachably connected to the diameter-increased part.

Here, the eyepiece section 232 is provided with a light source connector 2323 for connection of a light guide 2322. In other words, light supplied from the light guide 2322 of a light source device (omitted in illustration) is supplied to the insertion section 231 through the eyepiece section 232. The light supplied to the insertion section 231 is emitted from the tip of the insertion section 231, and is applied to the inside of the living body. The light applied to the inside of the living body and reflected by the inside of the living body (subject image) is emitted from the eyepiece section 232 through the optical system in the insertion section 231 and the eyepiece optical system 2321.

The resection electrode member 24 is inserted in and passed through the sheath 21 by way of the attaching member 221, and its tip projects from the tip of the sheath 21. The resection electrode member 24 has a tip portion making contact with the biomedical tissue, and treats the biomedical tissue by a high frequency current.

The handle section 25 is a part at which the doctor or the like grasps the resectoscope 2 and operates the resection electrode member 24. As depicted in FIG. 1, the handle section 25 includes a fixed ring 251, a slider 252, and a spring member 253.

The fixed ring 251 is a part on which the doctor or the like puts his or her thumb, and is fixed to the guide tube 22.

The slider 252 has the guide tube 22 inserted therein and passed therethrough, and is configured to be movable in the left-right direction in FIG. 1 along the guide tube 22. As depicted in FIG. 1, the resection electrode member 24 is fixed to the slider 252. In other words, the resection electrode member 24 is advanced and retracted in the left-right direction in FIG. 1 within the sheath 21, attendant on the movement of the slider 252. In addition, the slider 252 is provided with a power source connector 2522 for connection of a high-frequency power source cord 2521 connected to the high-frequency power source (omitted from illustration). The power source connector 2522 is electrically connected to the resection electrode member 24 through a lead wire (omitted from illustration). Further, as illustrated in FIG. 1, the slider 252 is provided with a finger-hooking member 2523 for the doctor or the like to hook a finger other than the thumb and to move the slider 252 (advance or retract the resection electrode member 24).

The spring member 253 is substantially U-shaped, has one end thereof attached to the fixed ring 251, and has the other end thereof attached to the slider 252. The spring member 253 biases the slider 252 toward the side spacing away from the fixed ring 251. In other words, the doctor or the like hooks his or her fingers on the fixed ring 251 and the finger-hooking member 2523, and draws near the finger-hooking member 2523 against the biasing force of the spring member 253, to thereby move the slider 252 toward the right side in FIG. 1 (to move the resection electrode member 24 toward the right side in FIG. 1). On the other hand, when the doctor or the like takes his or her finger off the finger-hooking member 2523, the slider 252 (the resection electrode member 24) is moved toward the left side in FIG. 1 by the biasing force of the spring member 253.

The endoscope imaging device 3 is detachably connected to the eyepiece section 232 of the resectoscope 2 (the endoscope 23). Under the control by the controller 5, the endoscope imaging device 3 images a subject image taken in by the endoscope 23 (a subject image emitted from the eyepiece section 232), and outputs an image signal (RAW signal) obtained by the imaging. The image signal is, for example, an image signal of 4K or more. Note that a detailed configuration of the endoscope imaging device 3 will be described later.

The display device 4 includes a display using liquid crystal, organic EL (Electro Luminescence), or the like. Under the control by the controller 5, the display device 4 displays an observation image based on a video signal from the controller 5.

The controller 5 includes a memory and a processor such as hardware of an FPGA (Field Programmable Gate Array) or a CPU (Central Processing Unit). The controller 5 integrally controls operations of the endoscope imaging device 3, the display device 4, and the power source device (omitted from illustration). For example, the controller 5 applies predetermined image processing to the image signal (RAW signal) outputted from the endoscope imaging device 3, to generate a video signal for display, and causes the display device 4 to display an observation image based on the video signal.

[Configuration of Endoscope Camera Head]

Next, a detailed configuration of an endoscope camera head 6 will be described. As depicted in FIG. 1, the endoscope camera head 6 and a cable 7 are provided.

The endoscope camera head 6 is a part detachably connected to the eyepiece section 232. As illustrated in FIG. 1, the endoscope camera head 6 includes a casing 8, a mount member 9 (coupler), a prism 10, a lens unit 11, and an imaging section 12.

The casing 8 is a housing that accommodates the prism 10, the lens unit 11, and the imaging section 12 therein.

The mount member 9 has in its inside a bottomed cylindrical shape in which the eyepiece section 232 can be fitted. The mount member 9 is restricted in movement in the direction of a first axis L1 relative to the casing 8, and can be rotated relative to the casing 8 with the first axis L1 as a center. Note that a detailed configuration of the mount member 9 will be described later.

The prism 10 is disposed on the first axis L1 and on an in-housing optical axis L2, and deflects the propagating direction of the subject image taken in by the endoscope 23. Specifically, the prism 10 deflects, by approximately 90°, the propagating direction of the subject image emitted from the eyepiece section 232 and taken into the casing 8 through an optical element (omitted from illustration), such that the subject image propagates along the in-housing optical axis L2.

The lens unit 11 is disposed on the in-housing optical axis L2. The lens unit 11 includes one or a plurality of lenses, and forms the subject image through the prism 10 on an imaging plane of the imaging section 12. In addition, the lens unit 11 is provided with an optical zoom mechanism (omitted from illustration) for changing the angle of view by moving one or a plurality of lenses, a focusing mechanism (omitted from illustration) for changing the focus, or the like, under the control by the controller 5 or an operation section 13.

The imaging section 12 is disposed on the in-housing optical axis L2. Further, the imaging section 12 images the subject image formed by the lens unit 11, under the control by the controller 5. The imaging section 12 includes a sensor chip in which an imaging element (omitted from illustration) such as a CCD (Charge Coupled Device) or a CMOS (Complementary Metal Oxide Semiconductor) for receiving the subject image formed by the lens unit 11 and converting it into an electrical signal, a signal processing section (omitted from illustration) for performing signal processing (A/D conversion or the like) on the electrical signal (analog signal) from the imaging element to output an image signal, and the like are integrally formed, and outputs an image signal obtained after A/D conversion (RAW signal (digital signal)). Note that the abovementioned signal processing section may not be integrally formed with the imaging element, and may be a separate body.

Thus, the endoscope camera head 6 is configured to be rotatable with the first axis L1 as a center relative to the eyepiece section 232 of the endoscope 23, through the mount member 9. In addition, the endoscope camera head 6 is configured such that the center of gravity O (FIG. 1) thereof is located at a position deviated from the first axis L1 (the rotational center axis for the eyepiece section 232). Further, the endoscope camera head 6 is rotated with the first axis L1 as a center, irrespectively of the rotation of the resectoscope 2 around the first axis L1, and is configured such that the in-housing optical axis L2 set in the casing 8 is normally in a posture along the vertical direction (a posture such that the center of gravity O is located on a lower side of the first axis L1).

The cable 7 has one end thereof detachably connected to the controller 5 through a connector CN1, and has the other end thereof detachably connected to the endoscope camera head 6 through a connector CN2. The cable 7 transmits an image signal outputted from the endoscope camera head 6, to the controller 5, and transmits control signals, a synchronizing signal, and clock outputted from the controller 5, electric power, and the like, to the endoscope camera head 6. Note that the transmission of the image signal from the endoscope camera head 6 to the controller 5 through the cable 7 may be transmission of the image signal in the form of an optical signal, or may be transmission of the image signal in the form of an electrical signal. This also applies to the transmission of the control signals, the synchronizing signal, and clock from the controller 5 to the endoscope camera head 6 through the cable 7. In addition, as depicted in FIG. 1, the cable 7 is provided with the operation section 13 that accepts various operations (for example, instructions of image quality adjustment of the observation image (white balance adjustment, brightness adjustment, etc.), instructions for changing the angle of view or focus of the lens unit 11, etc.) from the doctor or the like.

[Detailed Configuration of Mount Member]

Next, a detailed configuration of the mount member 9 will be described.

Figure 2:
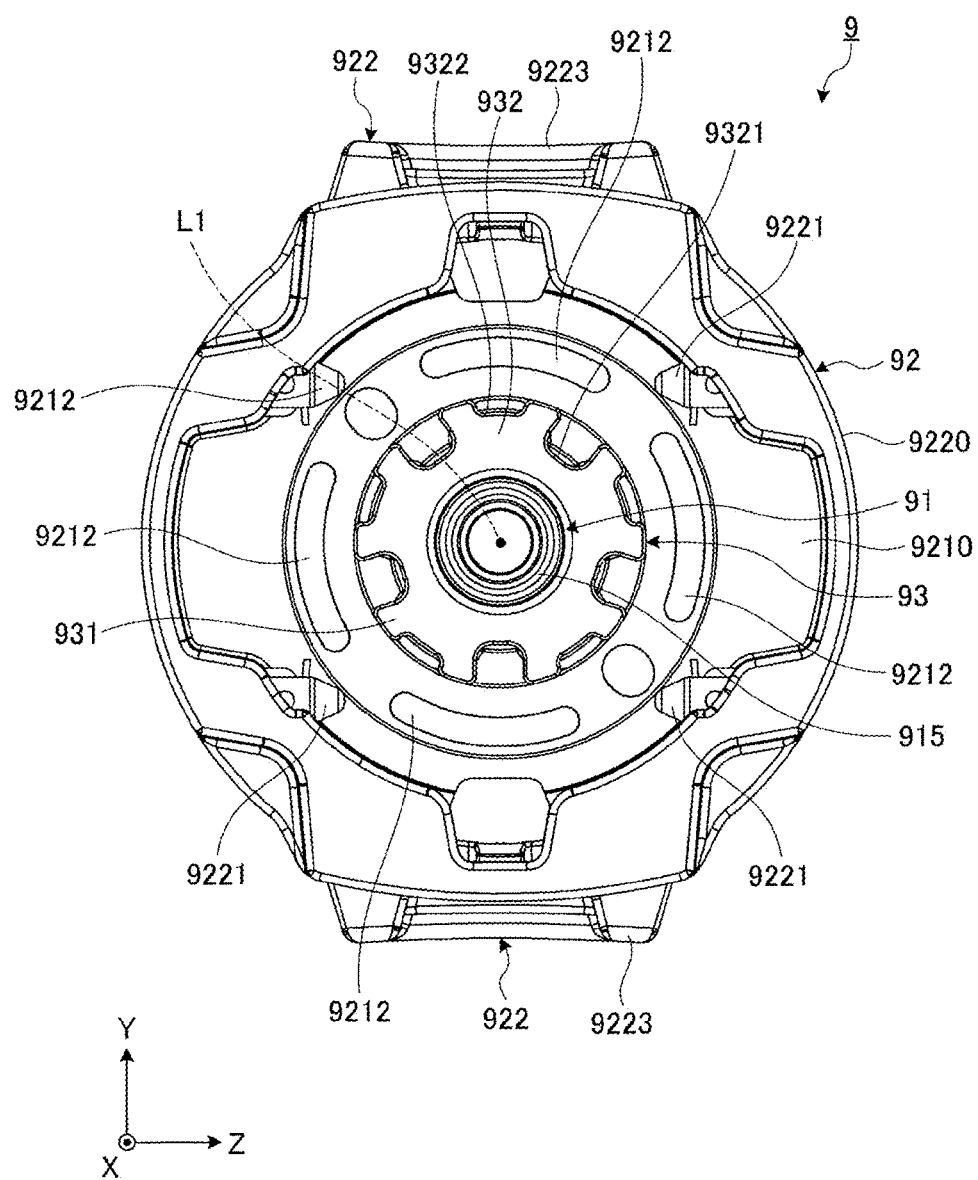
FIG. 2 is a front view of a mount member according to one embodiment.
Figure 3:
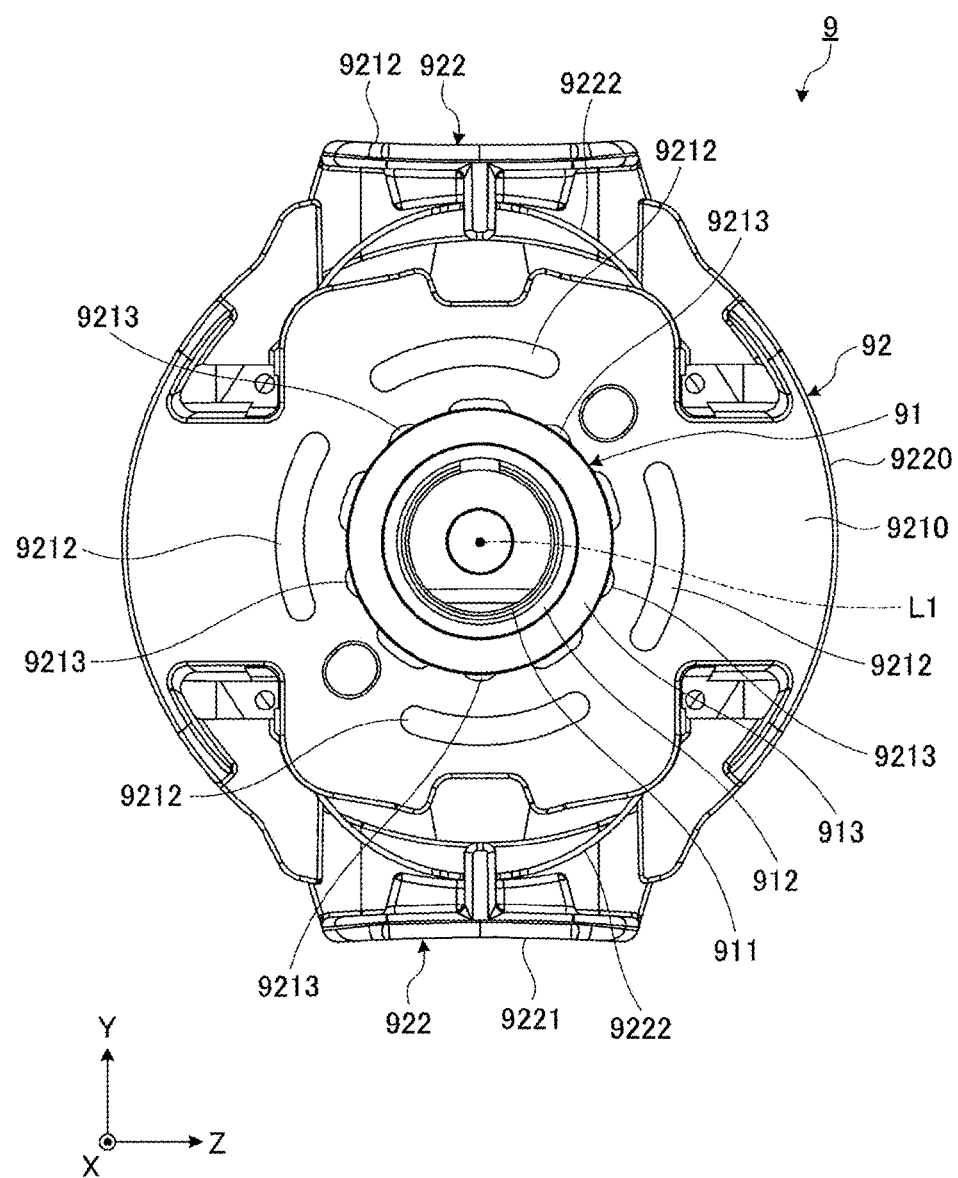
FIG. 3 is a back elevation of the mount member according to one embodiment.
Figure 4:
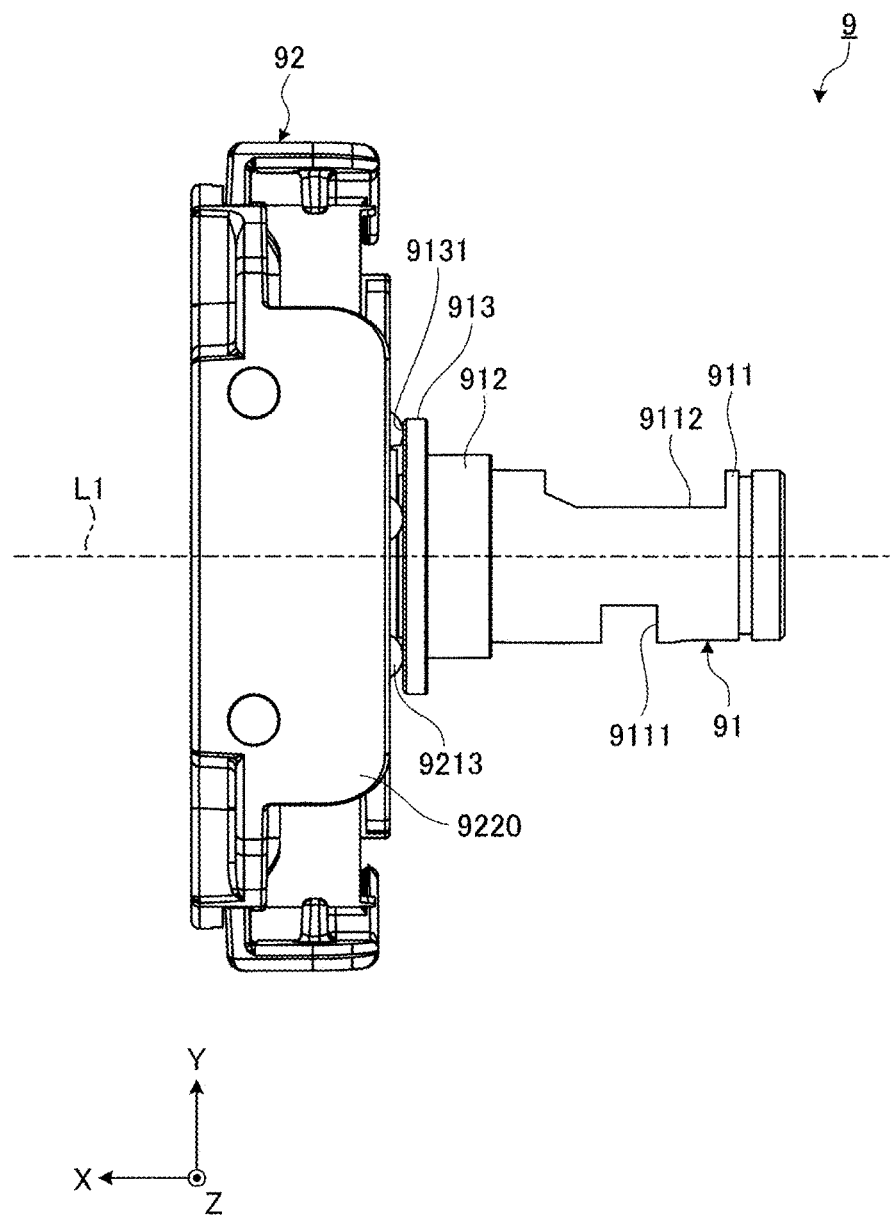
FIG. 4 is a side view of the mount member according to one embodiment.
Figure 5:
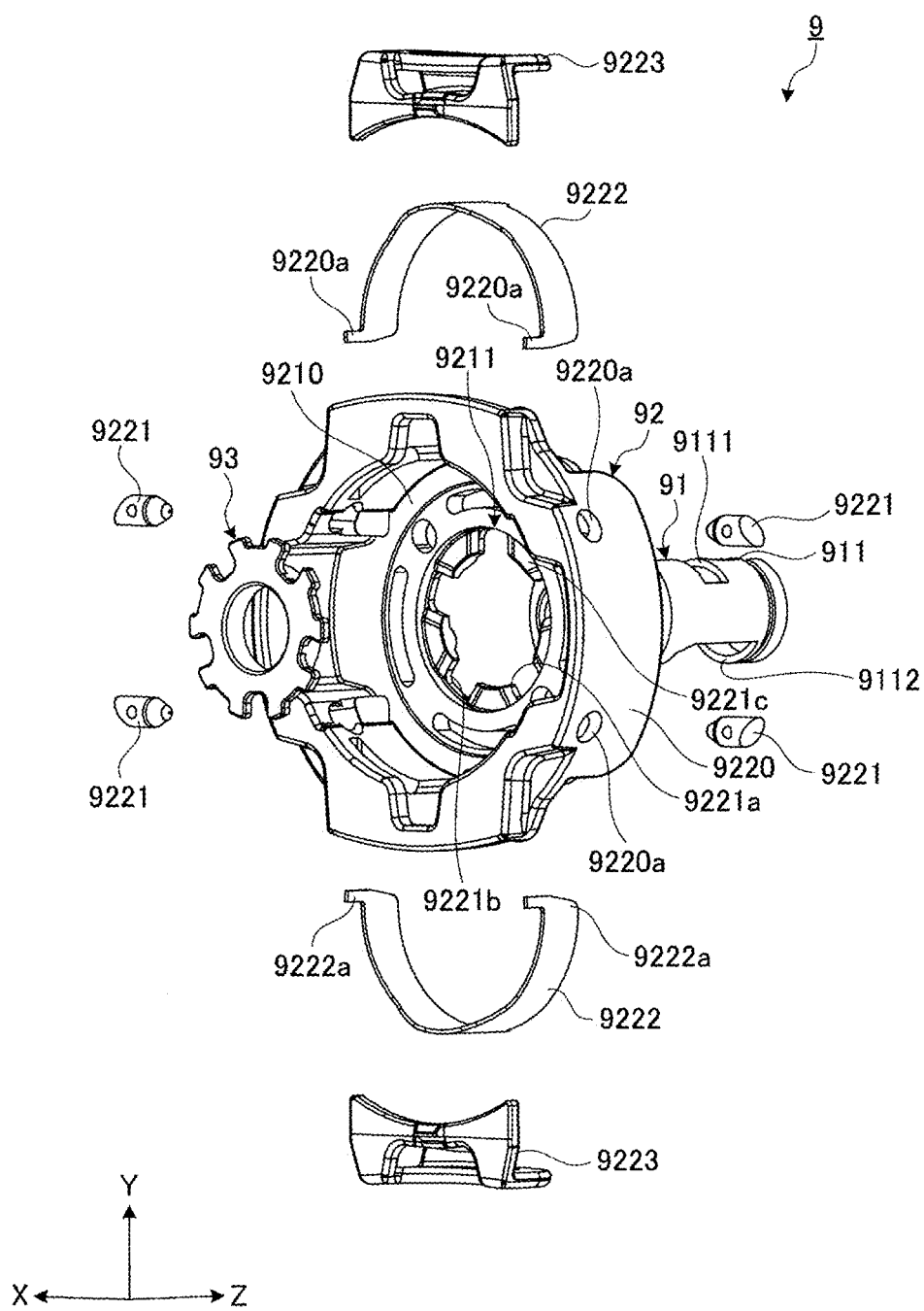
FIG. 5 is an exploded perspective view when the mount member according to one embodiment is viewed from the front side.
Figure 6:
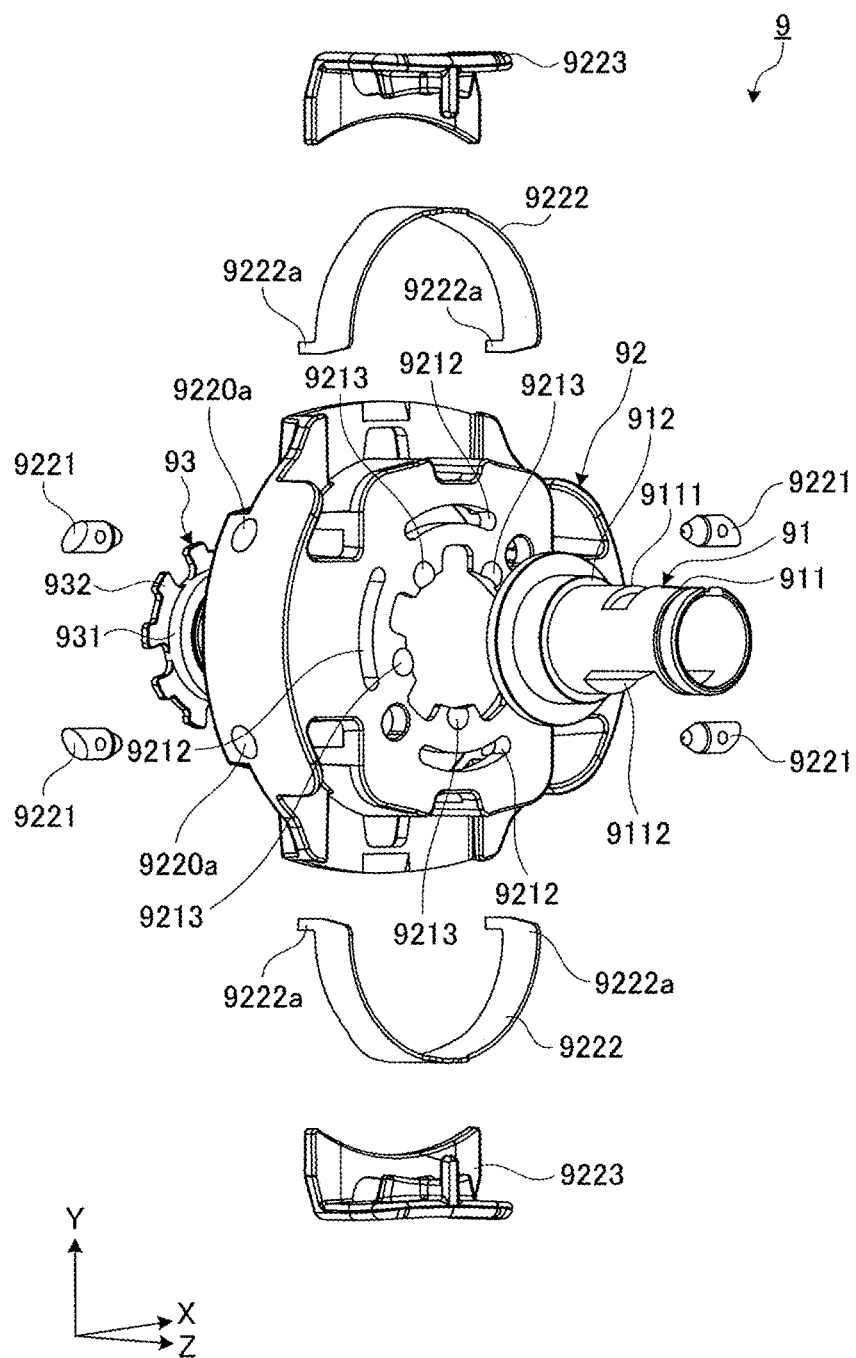
FIG. 6 is an exploded perspective view when the mount member according to one embodiment is viewed from the back side.

FIG. 2 is a front view of the mount member 9. FIG. 3 is a back elevation of the mount member 9. FIG. 4 is a side view of the mount member 9. FIG. 5 is an exploded perspective view when the mount member 9 is viewed from the front side. FIG. 6 is an exploded perspective view when the mount member 9 is viewed from the back side. Note that in FIGS. 2 to 6, for simplified explanation of the mount member 9, the casing 8 connected to the mount member 9 and the optical members accommodated in the mount member 9 are omitted.

As illustrated in FIGS. 2 to 6, the mount member 9 includes a first member 91, a second member 92, and a restriction member 93.

[Configuration of First Member]

First, a detailed configuration of the first member will be described.

Figure 7:
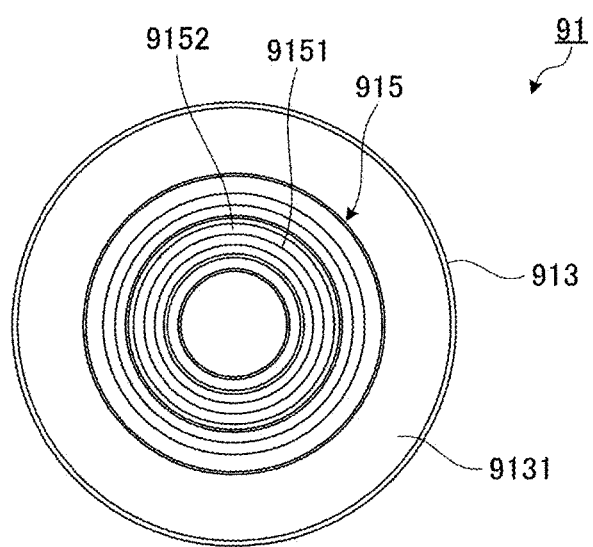
FIG. 7 is a front view of a first member according to one embodiment.
Figure 8:
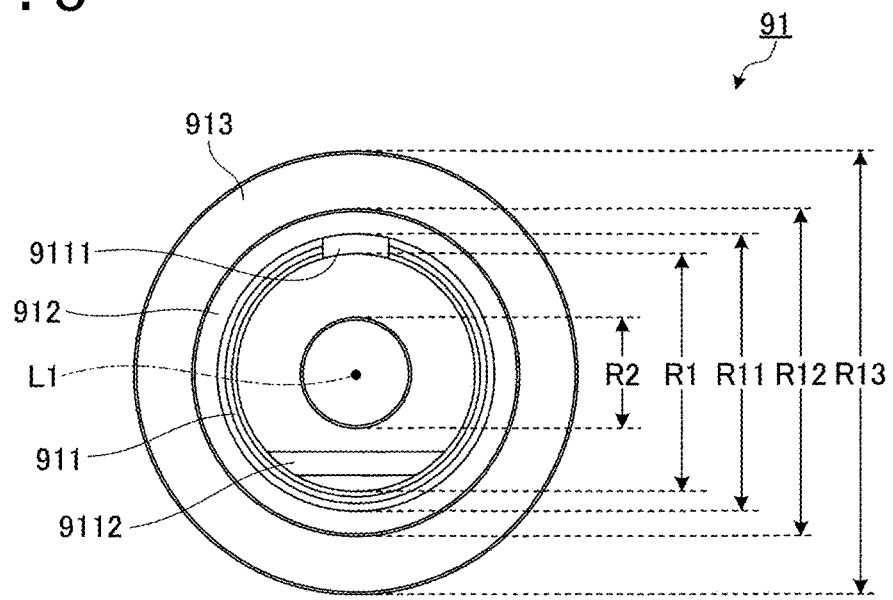
FIG. 8 is a back elevation of the first member according to one embodiment.
Figure 9:
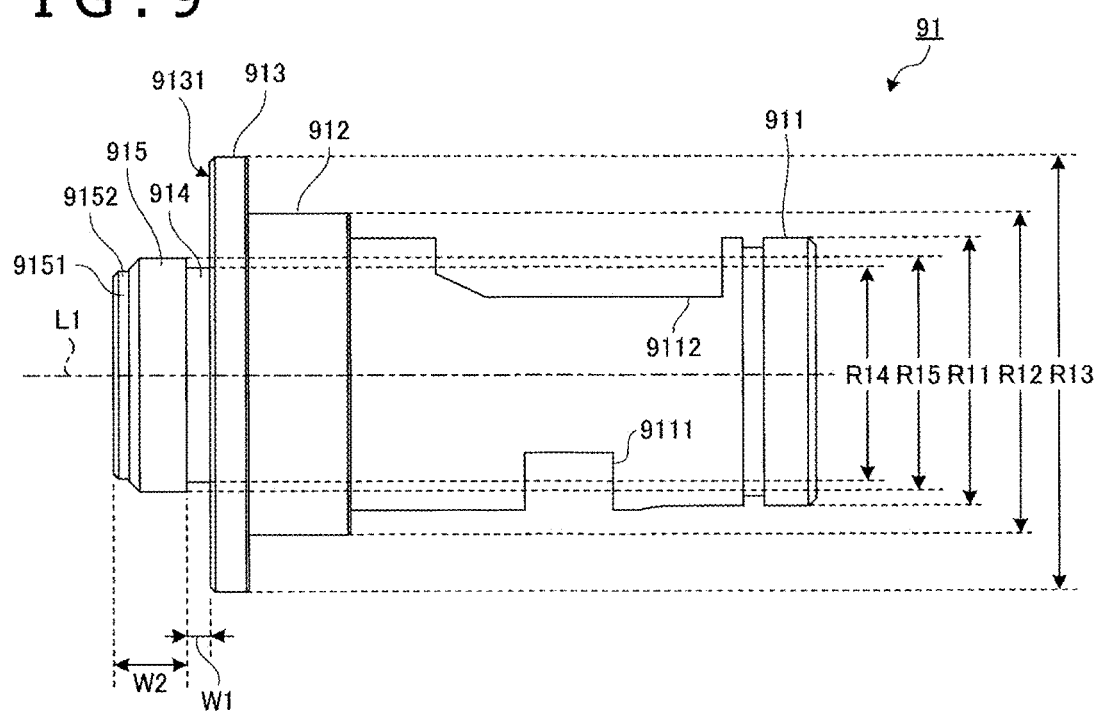
FIG. 9 is a side view of the first member according to one embodiment.

FIG. 7 is a front view of the first member 91. FIG. 8 is a back elevation of the first member 91. FIG. 9 is a side view of the first member 91.

As depicted in FIGS. 2 to 6 and FIGS. 7 to 9, the first member 91 is provided in the endoscope camera head 6 having the imaging section 12. Specifically, the first member 91 is a member for attaching the mount member 9 to the casing 8, and a member for supporting rotation of the second member 92. The first member 91 includes a first main body section 911, a second main body section 912, a third main body section 913, a fourth main body section 914, and a fifth main body section 915. The first main body section 911, the second main body section 912, the third main body section 913, the fourth main body section 914, and the fifth main body section 915 are integrally formed by resin molding or the like.

The first main body section 911 has a tubular shape having an inside diameter R1 with the first axis L1 as a center. The first main body section 911 accommodates an optical member (omitted from illustration) therein. The first main body section 911 has a first opening 9111 and a second opening 9112 at opposite positions of side surfaces orthogonal to the first axis L1. The first opening 9111 and the second opening 9112 are different from each other in size of the opening.

The second main body section 912 is provided to extend in an annular shape with the first axis L1 as a center, and has an inside diameter R2. In addition, the second main body section 912 has an outside diameter R12 greater than an outside diameter R11 of the first main body section 911 (R11<R12).

The third main body section 913 is provided to extend in an annular shape with the first axis L1 as a center, and has the inside diameter R2. The third main body section 913 has an outside diameter R13 greater than the outside diameter R12 of the second main body section 912 (R11<R12<R13). The third main body section 913 has a contact surface 9131 making contact with a back surface 9210a of a bottom section 9210 of the second member 92 described later, in the direction of the first axis L1 (the left side in FIG. 9). Note that, in one embodiment, the contact surface 9131 functions as a first rotational sliding surface.

The fourth main body section 914 is provided to extend in an annular shape with the first axis L1 as a center, and has the inside diameter R2. The fourth main body section 914 has an outside diameter R14 smaller than the outside diameter R11 of the first main body section 911. In addition, the fourth main body section 914 is formed such that a length W1 in the direction along the first axis L1 is approximately equal to a length W11 of a spacing-apart section 9213 provided on the back surface 9210a side of the bottom section 9210 of the second member 92 described later.

The fifth main body section 915 is provided to extend in an annular shape with the first axis L1 as a center, and has the inside diameter R2. The fifth main body section 915 has an outside diameter R15 smaller than the outside diameter R11 of the first main body section 911 but greater than the outside diameter R14 of the fourth main body section 914 (R14<R15<R11). In addition, the fifth main body section 915 is formed such that a length W2 in the direction along the first axis L1 is approximately equal to a thickness W10 of the bottom section 9210 of the second member 92 described later. Further, the fifth main body section 915 has, on the outer circumferential side of a tip section 9151, a screw groove section 9152 capable of screw engagement with the restriction member 93 described later.

[Configuration of Second Member]

Next, a detailed configuration of the second member 92 will be described.

Figure 10:
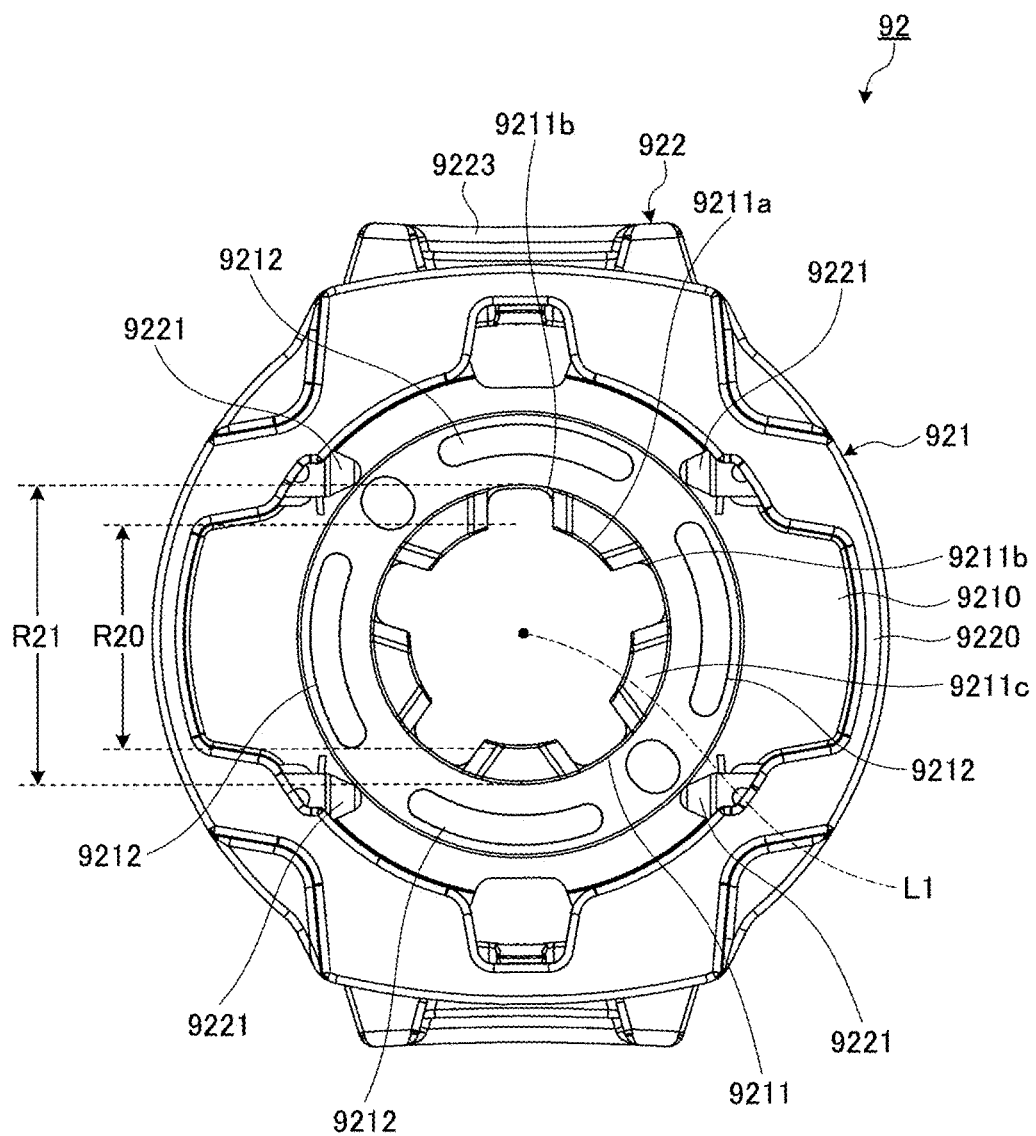
FIG. 10 is a front view of a second member according to one embodiment.
Figure 11:
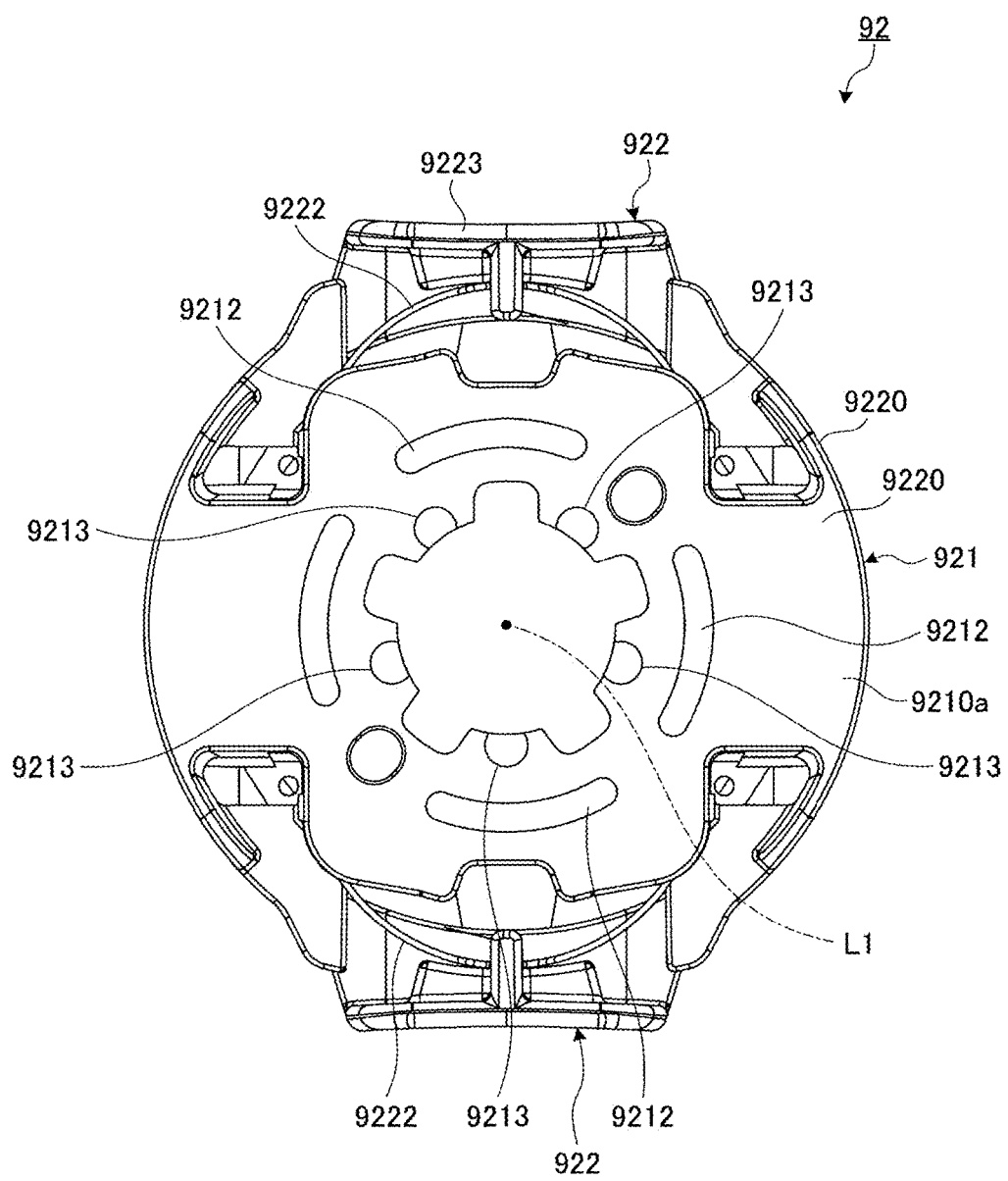
FIG. 11 is a back elevation of the second member according to one embodiment.
Figure 12:
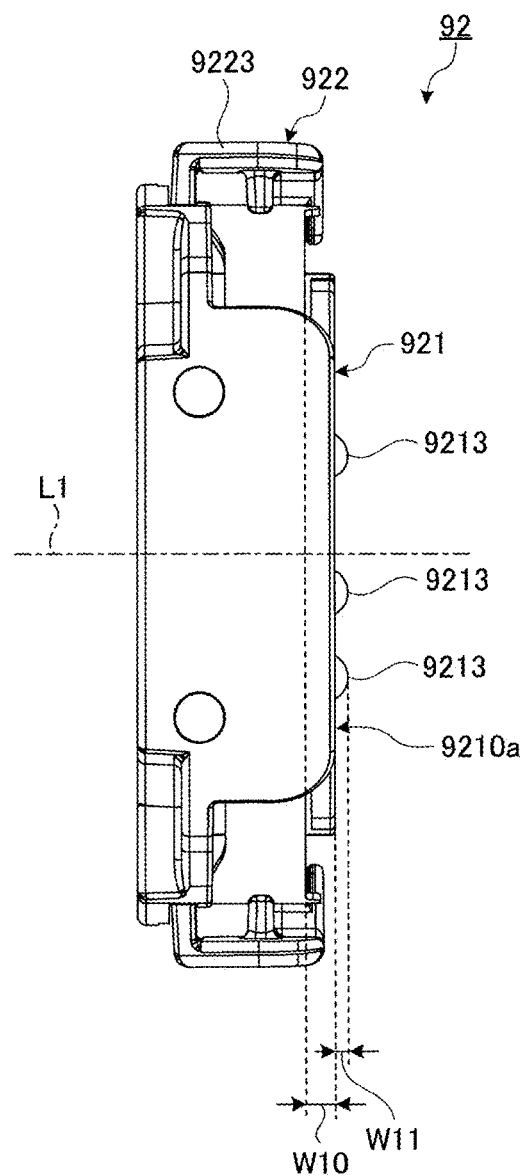
FIG. 12 is a side view of the second member according to one embodiment.

FIG. 10 is a front view of the second member 92. FIG. 11 is a back elevation of the second member 92. FIG. 12 is a side view of the second member 92.

As illustrated in FIGS. 2 to 6 and FIGS. 10 to 12, the second member 92 is rotatable around the first axis L1 passing through the first member 91, and the endoscope 23 is connectable thereto. The second member 92 has a tubular section 921 and a pressing section 922.

The tubular section 921 has a bottomed tubular shape in which the eyepiece section 232 can be fitted. The tubular section 921 has a disk-shaped bottom section 9210 and a wall section 9220 that extends toward the front side along the first axis L1 from an outer edge of the bottom section 9210.

The bottom section 9210 has the thickness W10 along the first axis L1 approximately equal to a thickness W2 of the fifth main body section 915 of the first member 91. In addition, the bottom section 9210 has a contact section 9211, a slot 9212, and a spacing-apart section 9213.

An inside diameter R21 of the contact section 9211 is approximately equal to an outside diameter R30 of the restriction member 93 described later. In addition, the contact section 9211 is formed with a through-hole 9211a which penetrates the contact section 9211 from the face to the back and which has a circular plan-view shape having an inside diameter R20 approximately equal to the outside diameter R14 of the fourth main body section 914 of the first member 91, and the contact section 9211 is rotatable in a state in which the first member 91 is inserted in the through-hole 9211a. Further, the contact section 9211 has at least one cutout 9211b formed to be cut out from the outer circumferential side of the through-hole 9211a toward the outer edge side of the contact section 9211; and an end part 9211c of which the front surface side makes contact with the back surface side of the restriction member 93.

Figure 13:
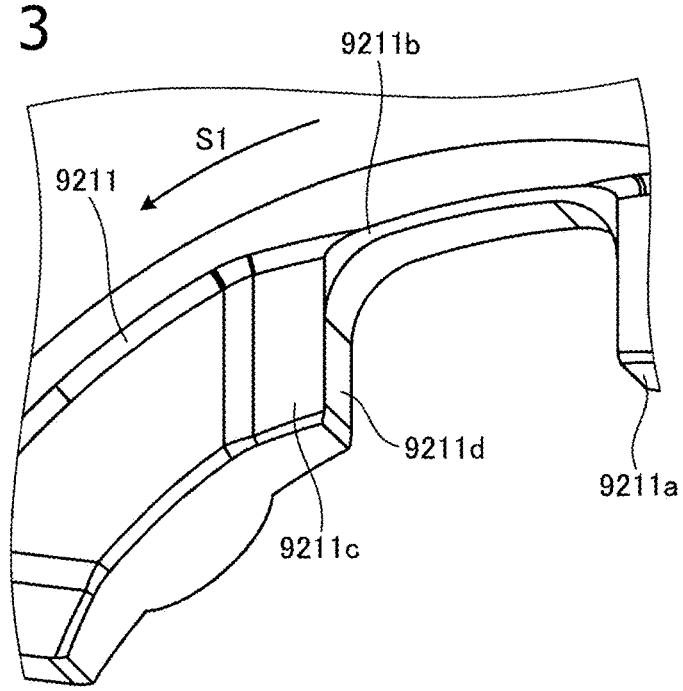
FIG. 13 is an enlarged view in which a part of the second member according to one embodiment is enlarged.

The cutouts 9211b are provided at a plurality of sites, for example, at five sites, at a predetermined angular interval with the first axis L1 as a center. The cutouts 9211b have undergone R processing such as to be rounded toward the outer edge side of the bottom section 9210. In addition, as depicted in FIG. 13, the cutouts 9211b may be such that end faces 9211d of the end parts 9211c of the cutouts 9211b are tapered to be inclined toward the rotating direction S1 of the second member 92. Note that, other than the tapered shape, the end part 9211c may be such that the front surface side of the end part 9211c has a shape inclined at a certain angle toward the rotating direction S1 of the second member 92 or a rounded shape. Besides, in one embodiment, the cutout 9211b functions as a second cutout.

The slot 9212 extends in the shape of an arc of a circle with the first axis as a center, and penetrates from the face side to the back side. The slots 9212 are provided at a plurality of sites, for example, at four sites, at a predetermined interval in the bottom section 9210.

The spacing-apart sections 9213 are provided in plural numbers on the back surface 9210a side of the contact section 9211 of the bottom section 9210. Specifically, the spacing-apart sections 9213 are provided on the back surface 9210a side of the bottom section 9210 and on the back surface side of the contact section 9211 at, for example, five sites along the circumferential direction of the second member 92 at a predetermined interval. The spacing-apart sections 9213 project to the back surface side along the first axis L1, and are formed in a hemispherical shape.

The pressing section 922 presses the endoscope 23 toward the first axis L1 when the endoscope 23 is connected to the second member 92. The pressing section 922 has such elasticity as to be movable in the direction for approaching or spacing away from the first axis L1 of the mount member 9, and makes contact with an outer circumferential surface of the eyepiece section 232 fitted inside the mount member 9, to press the eyepiece section 232 toward the bottom section 9210 of the mount member 9. The pressing section 922 has pressing members 9221, elastic members 9222, and support members 9223.

The pressing members 9221 are inserted in a movable manner in each of four holes 9220a provided in a wall section 9220 as an object of rotation by 90° with the first axis L1 of the mount member 9 as a center.

The elastic members 9222 include curved leaf springs or the like, and are mounted to the wall section 9220 through the support members 9223. The elastic member 9222 biases the pressing members 9221 toward the first axis L1 of the mount member 9, with the pressing members 9221 making contact with both end parts 9222a of the elastic member 9222.

The support members 9223 exert a pressing force externally given toward the first axis L1 of the mount member 9 on the elastic members 9222, whereby the elastic members 9222 are spread to the outer circumferential side of the wall section 9220, and the biasing of the pressing members 9221 by the elastic members 9222 is cancelled. As a result, the eyepiece section 232 can easily be detached from the mount member 9.

[Configuration of Restriction Member]

Next, a detailed configuration of the restriction member 93 will be described.

Figure 14:
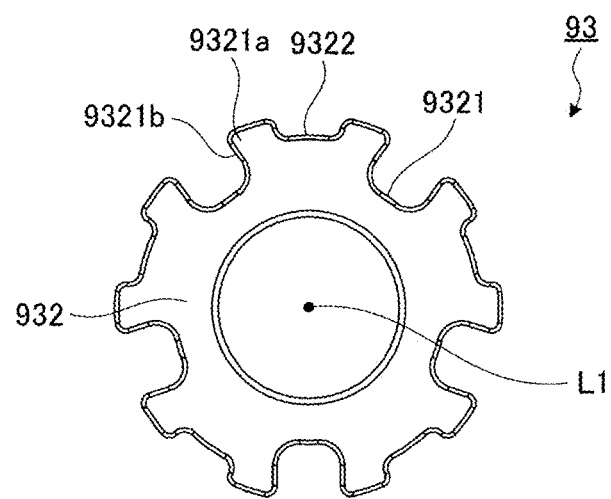
FIG. 14 is a front view of a restriction member according to one embodiment.
Figure 15:
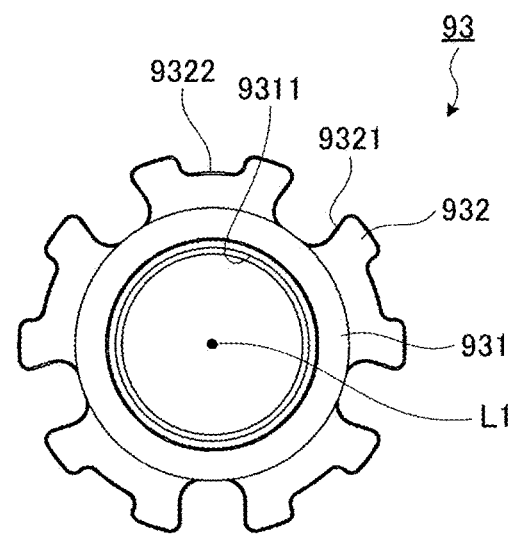
FIG. 15 is a back elevation of the restriction member according to one embodiment.
Figure 16:
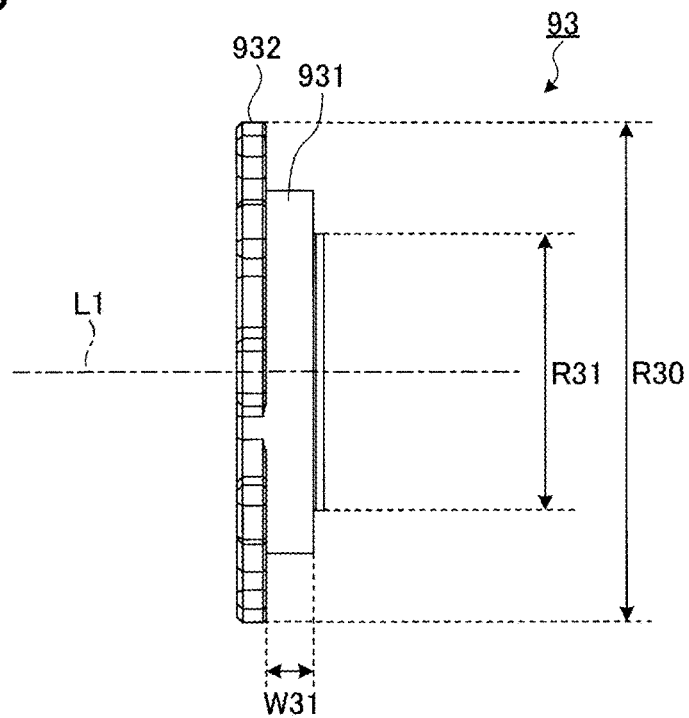
FIG. 16 is a side view of the restriction member according to one embodiment.

FIG. 14 is a front view of the restriction member 93. FIG. 15 is a back elevation of the restriction member 93. FIG. 16 is a side view of the restriction member 93.

As depicted in FIGS. 2 to 6 and FIGS. 14 to 16, the restriction member 93 restricts the second member 92 from moving in the direction of the first axis L1, by clamping the second member 92 in a manner allowing rotation, through the first member 91. The restriction member 93 has a main body section 931 and a flange section 932. The main body section 931 and the flange section 932 are formed integrally.

The main body section 931 has a tubular shape with the first axis L1 as a center, and has an inside diameter R31 approximately equal to the outside diameter R14 of the fourth main body section 914 of the first member 91. In addition, the main body section 931 has a thickness W31 along the first axis L1 direction approximately equal to the thickness W10 of the bottom section 9210. The main body section 931 is fitted to the fourth main body section 914. Further, the main body section 931 is provided, on the inner circumferential side thereof, with a screw groove 9311.

The flange section 932 has an outside diameter R30 approximately equal to the inside diameter R21 of the contact section 9211. The flange section 932 has at least one cutout 9321 and cutout 9322 formed such as to expose, to the exterior, a part of the end part 9211c making contact with the second member 92. Note that, in one embodiment, the cutout 9321 functions as a first cutout.

The cutout 9321 is formed by being cut out from an outer edge side toward the first axis L1. Note that an end face 9321b of an end part 9321a of the cutout 9321 may be formed in a tapered shape inclined toward the rotating direction of the second member 92, or may be formed in a shape formed with a predetermined angle or a rounded shape.

Figure 17:
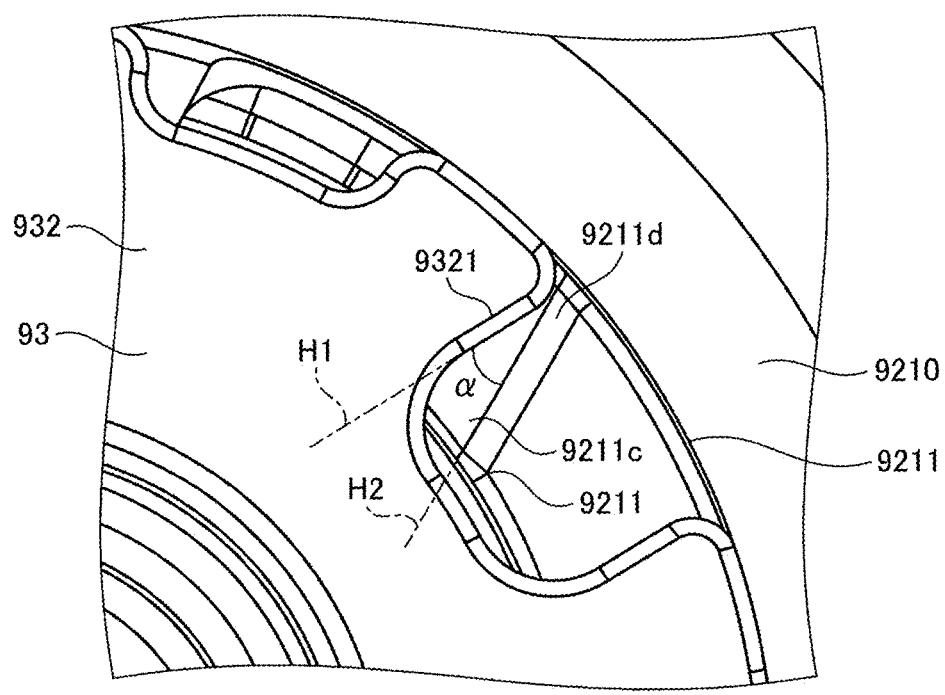
FIG. 17 is an enlarged view in which a part of the mount member according to one embodiment at the time of operation is enlarged.

The mount member 9 configured in such a way restricts the second member 92 from moving in the direction of the first axis, by clamping the second member 92 in a manner allowing rotation, by the restriction member 93 through the first member 91. Further, the mount member 9 is configured such that the cutout 9321 (first cutout) of the restriction member 93 exposes, to the exterior, a part (end part 9211c) of the contact section 9211 of the second member 92 clamped through the first member 91. Further, as depicted in FIG. 17, the mount member 9 is configured such that the end part 9321a of the cutout 9321 (first cutout) of the restriction member 93 and the end part 9211c of the cutout 9211b (second cutout) of the second member 92 intersect each other, in a case where the cutout 9211b of the second member 92 and the cutout 9321 of the restriction member 93 overlap with each other, in a state in which the second member 92 is rotated. For example, as depicted in FIG. 17, the mount member 9 is configured such that an angle a formed between the cutout 9321 (straight line H1) of the restriction member 93 and the cutout 9211b (straight line H2) of the second member 92 is an acute angle, in a case where the cutout 9211b of the second member 92 and the cutout 9321 of the restriction member 93 overlap with each other, in a state in which the second member 92 is rotated. In other words, since the cutout 9321 of the restriction member 93 and the cutout 9211b of the second member 92 are each rotated (enter) with an angle relative to each other, the restriction member 93 and the second member 92 can be prevented from colliding against each other at the time of rotation. As a result, the mount member 9 has the second member 92 smoothly rotated relative to the first axis L1.

Figure 18:
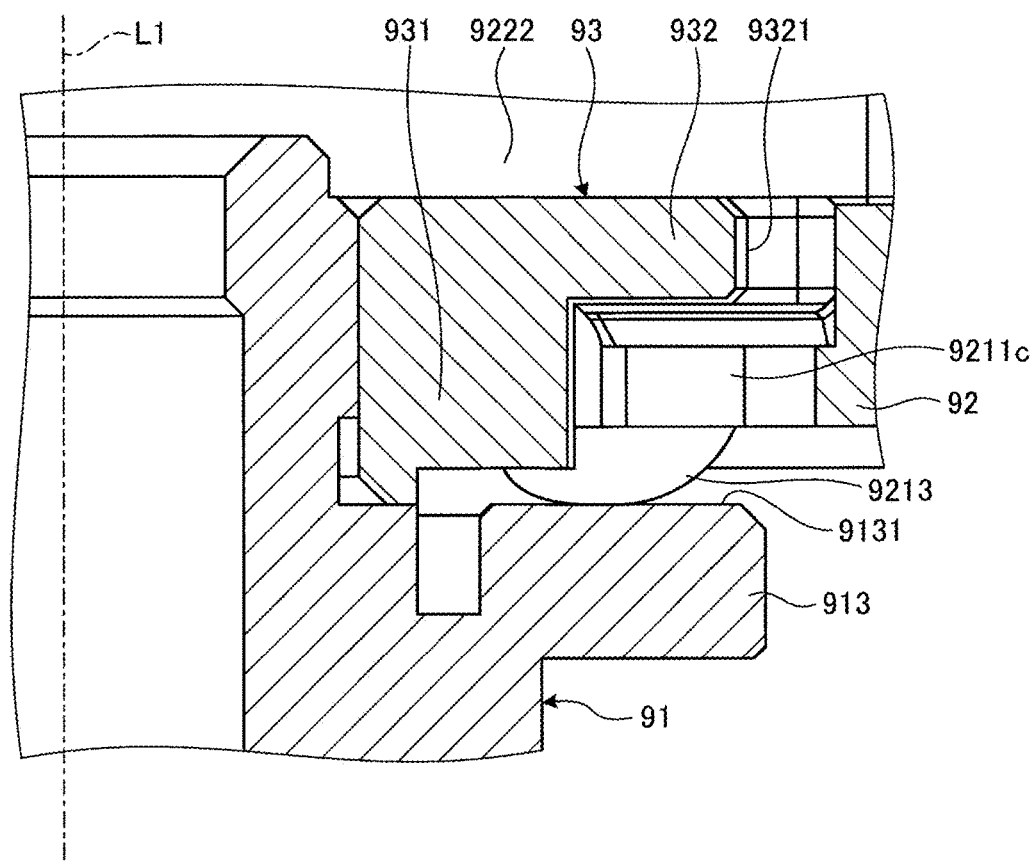
FIG. 18 is an enlarged view in which a cross section of a part of the mount member according to one embodiment is enlarged.

In addition, as depicted in FIG. 18, since the contact area between the spacing-apart section 9213 provided in the second member 92 and the contact surface 9131 of the first member 91 can be reduced to a minimum, the second member 92 can be smoothly rotated relative to the first axis L1.

[Cleaning of Mount Member]

Figure 19A:
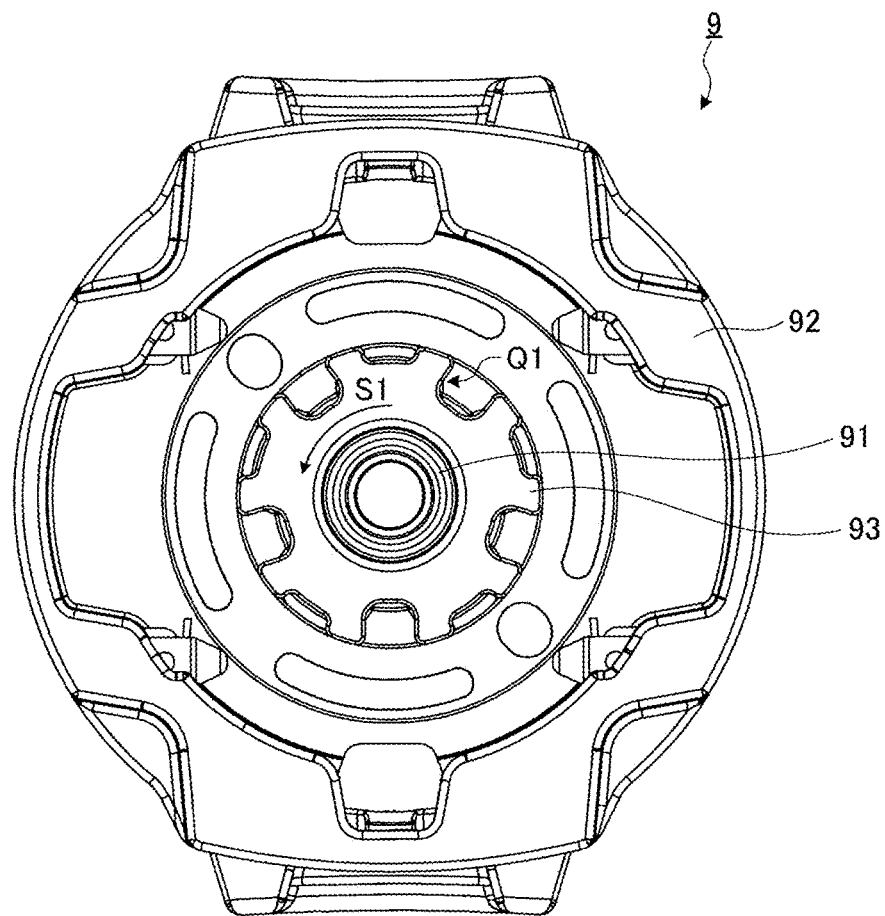
FIG. 19A is a diagram for schematically explaining an operation conducted at the time of cleaning the mount member according to one embodiment.
Figure 19B:
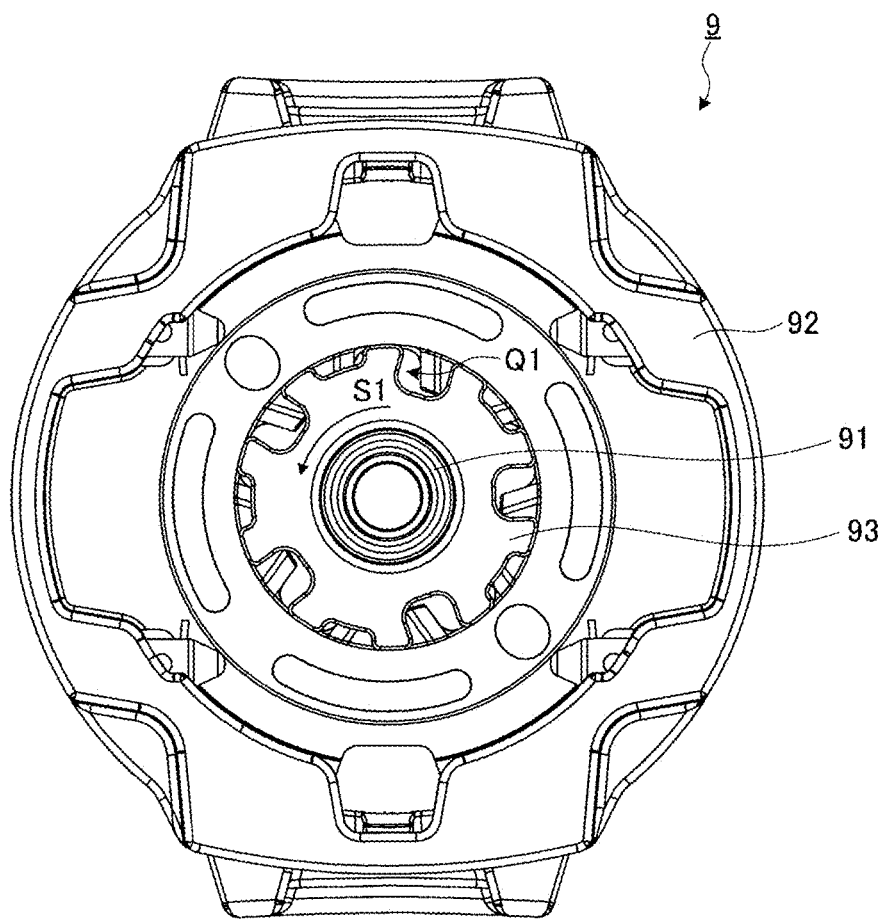
FIG. 19B is a diagram for schematically explaining an operation conducted at the time of cleaning the mount member according to one embodiment.
Figure 19C:
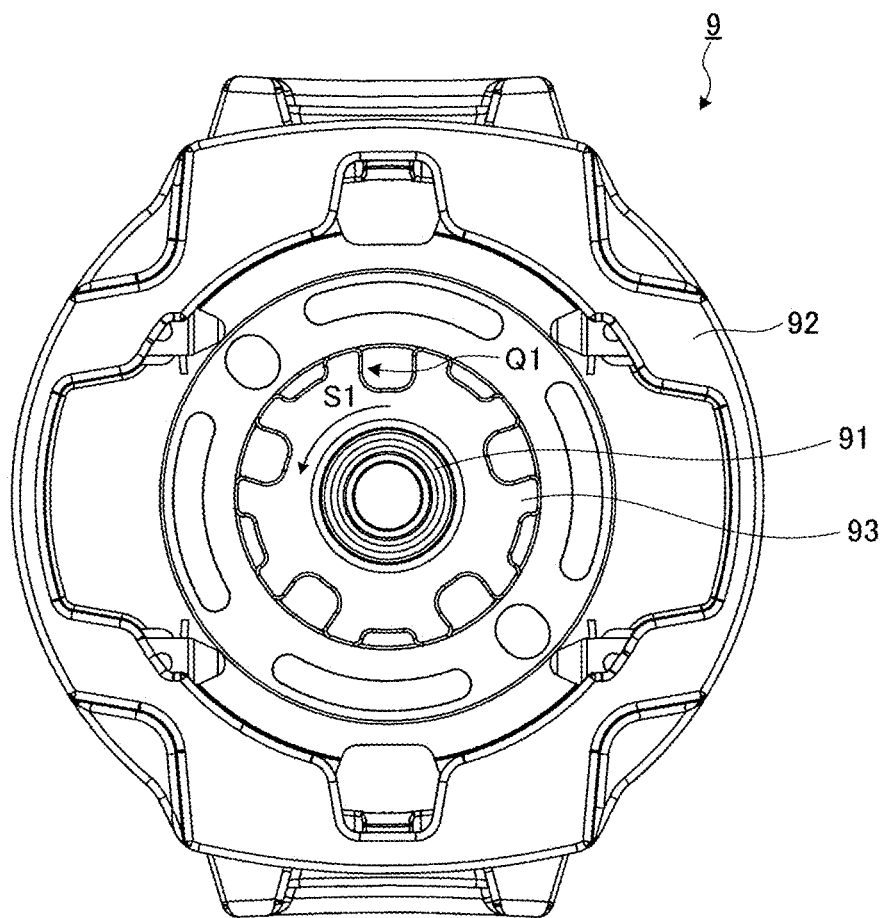
FIG. 19C is a diagram for schematically explaining an operation conducted at the time of cleaning the mount member according to one embodiment.

Next, a cleaning method for the mount member 9 will be described. FIGS. 19A to 19C are diagrams for schematically explaining an operation at the time of cleaning the mount member 9.

In a case of rotating the second member 92 (FIG. 19(A)→FIG. 19(B)→FIG. 19(C)) as depicted in FIG. 19A, the contact section 9211 of the second member 92 is sequentially exposed by the cutout 9321 of the restriction member 93 and by the cutout 9321 of the second member 92, and a cleaning liquid Q1 flows in, so that the contact section 9211 of the second member 92 can be cleaned. Further, since an edge of the contact section 9211 of the second member 92 is also exposed, the edge part can also be cleaned. Furthermore, since the cleaning liquid Q1 having flowed in from the front surface side flows in from the front surface side to the back surface side through the cutout 9321 of the restriction member 93 and the cutout 9211b of the second member 92, cleaning efficiency can be enhanced.

According to one embodiment described above, the restriction member 93 has at least one cutout 9321 cut out such as to expose, to the exterior, a part of the contact section 9211 of the second member 92 clamped through the first member 91, and the contact section 9211 can be exposed to the exterior by mere rotation of the second member 92, and thus, the length of cleaning time of the mount member 9 can be shortened.

In addition, according to one embodiment, since the second member 92 is formed with the cutout 9211b, the cleaning liquid Q1 having flowed in from the front surface side flows in from the front surface side to the back surface side through the cutout 9321 of the restriction member 93 and the cutout 9211b of the second member 92, and thus, cleaning efficiency can be enhanced.

Besides, according to one embodiment, in the case where the cutout 9211b of the second member 92 and the cutout 9321 of the restriction member 93 overlap with each other in a state in which the second member 92 is rotated, the end part 9321a of the cutout 9321 of the restriction member 93 and the end part 9211c of the cutout 9211b of the second member 92 intersect each other, and thus, the second member 92 can be smoothly rotated relative to the first axis L1.

In addition, according to one embodiment, since the tapered shape inclined toward the rotating direction S1 from the end face 9211d of the end part 9211c of the cutout 9211b of the second member 92 is provided, the second member 92 can be smoothly rotated with the first axis L1 as a center.

Besides, according to one embodiment, since the spacing-apart section 9213 is provided on the back surface 9210a side of the second member 92, the second member 92 can be smoothly rotated with the first axis L1 as a center.

In addition, according to one embodiment, since the second member 92 is provided with at least one slot 9212 extending in the form of an arc of a circle with the first axis L1 as a center, steam generated inside the mount member 9 can be exhausted to the exterior, even in a case where the cutout 9211b of the second member 92 and the cutout 9321 of the restriction member 93 overlap with each other in a state in which the second member 92 is rotated.

Note that, while the spacing-apart section 9213 has been provided on the back surface 9210a side of the second member 92 in one embodiment, the spacing-apart section 9213 may be provided at the contact surface 9131 (first rotational sliding surface) of the first member 91, for example.

In addition, in the medical observation system according to one embodiment of the present disclosure, the abovementioned term "section" can be replaced by "means" or a "circuit." For example, the control section can be replaced by control means or a control circuit.

While some embodiments of the present application have been described in detail based on the drawings, these are merely examples, and the present invention can be carried out not only by the embodiments described in the disclosure of the invention but also in other modes obtained through various modifications or improvements based on the knowledge of those skilled in the art.

Note that the present technology can also take the following configurations.

(Additional Remark 1)

A mount member including:

a first member provided in a camera head having an imaging section;

a second member that is rotatable around a first axis passing through the first member and to which an endoscope is connectable; and a restriction member that restricts the second member from moving in the first axis direction, by clamping the second member in a manner allowing rotation, through the first member, and that has at least one first cutout cut out such as to expose, to an exterior, a part of a contact section of the second member clamped through the first member.

(Additional Remark 2)

The mount member according to (Additional Remark 1), in which the contact section
is formed with a through-hole in which the first member is to be inserted, and is rotatable in a state in which the first member is inserted in the through-hole, and
has at least one second cutout cut out toward an outer edge side of the contact section from an outer circumferential side of the through-hole.

(Additional Remark 3)

The mount member according to (Additional Remark 2), in which the first cutout and the second cutout are formed such that an end part of the first cutout and an end part of the second cutout intersect each other in a case where the end part of the first cutout and the end part of the second cutout overlap with each other.

(Additional Remark 4)

The mount member according to (Additional Remark 2) or (Additional Remark 3),
in which the first cutout and the second cutout are formed such that at least one of the end part of the first cutout and the end part of the second cutout is in a tapered shape inclined toward a rotating direction from the end face.

(Additional Remark 5)

The mount member according to any one of (Additional Remark 2) to (Additional Remark 4), including:
a spacing-apart section that spaces apart the first member and the second member,
in which the first member has a first rotational sliding surface that clamps the contact section through the second member, and the spacing-apart section is provided at either one of the first rotational sliding surface and a surface on the first rotational sliding surface side of the contact section.

(Additional Remark 6)

The mount member according to any one of (Additional Remark 2) to (Additional Remark 5), in which the second member has at least one slot that extends in a shape of an arc of a circle with the first axis as a center.

(Additional Remark 7)

An endoscope device including:

the mount member according to claim 1; and an endoscope that takes in an image of a subject and emits the image, in which the second member includes a pressing section that presses the endoscope toward the first axis when the endoscope is connected to the second member.

REFERENCE SIGNS LIST

1: Endoscope device
2: Resectoscope
3: Endoscope imaging device
4: Display device
5: Controller
6: Endoscope camera head
7: Cable
8: Casing
9: Mount member
10: Prism
11: Lens unit
12: Imaging section
13: Operation section
21: Sheath
22: Guide tube
23: Endoscope
24: Resection electrode member
25: Handle section
91: First member
92: Second member
93: Restriction member
911: First main body section
912: Second main body section
913: Third main body section
914: Fourth main body section
915: Fifth main body section
921: Tubular section
922: Pressing section
931: Main body section
932: Flange section
9131: Contact surface
9210: Bottom section
9210a: Back surface
9211: Contact section
9211a: Through-hole
9211b, 9321, 9322: Cutout
9211c, 9321a: End part
9211d, 9321b: End face
9212: Slot
9213: Spacing-apart section
9220: Wall section
9220a: Hole
9221: Pressing member
L1: First axis
L2: In-housing optical axis
Q1: Cleaning liquid

The invention claimed is:

1. A mount comprising:
a first member provided in a camera head having an imaging sensor;
a second member that is rotatable relative to the first member around a first axis passing through the first member and to which an endoscope is connectable; and
a restriction member that is configured to clamp the second member to restrict the second member from moving along the first axis, while allowing rotation of the second member around the first axis relative to the first member, wherein the restriction member has at least one first cutout that exposes, to an exterior, a part of a contact section of the second member while the second member is clamped to the first member.

2. The mount according to claim 1,
wherein the contact section of the second member includes
a through-hole in which the first member is to be inserted, and is rotatable while the first member is inserted in the through-hole, and
at least one second cutout that extends from an outer circumferential side of the through-hole.

3. The mount according to claim 2,
wherein the first cutout and the second cutout are each defined by an end part and an end face on either side of a bottom face thereof, wherein an end part of the first cutout and an end part of the second cutout intersect each other when the end part of the first cutout and the end part of the second cutout overlap.

4. The mount according to claim 3,
wherein at least one of the end part of the first cutout and the end part of the second cutout is in a tapered shape.

5. The mount according to claim 3, comprising:
a spacer that spaces apart the first member and the second member,
wherein the first member has a first rotational sliding surface closest to the contact section of the second member, and
the spacer is provided at either one of the first rotational sliding surface and the contact section.

6. The mount according to claim 5, wherein the spacer extends from one of the first rotational sliding surface and the contact section and has a curved surface facing another one of the first rotational sliding surface and the contact section.

7. The mount according to claim 5, wherein the spacer includes a plurality of spacers between the first member and the second member.

8. The mount according to claim 3,
wherein the second member has at least one slot that extends in a shape of an arc of a circle with the first axis as a center.

9. The mount according to claim 3, wherein an end face of the first cutout and an end face of the second cutout form an acute angle when the end part of the first cutout and the end part of the second cutout overlap.

10. The mount according to claim 2,
wherein the first cutout and the second cutout are each defined by an end part and an end face on either side of a bottom face thereof, wherein at least one of an end part of the first cutout and an end part of the second cutout is in a tapered shape.

11. The mount according to claim 10, comprising:
a spacer that spaces apart the first member and the second member,
wherein the first member has a first rotational sliding surface closest to the contact section of the second member, and
the spacer is provided at either one of the first rotational sliding surface and the contact section.

12. The mount according to claim 11, wherein the spacer extends from one of the first rotational sliding surface and the contact section and has a curved surface facing another one of the first rotational sliding surface and the contact section.

13. The mount according to claim 10,
wherein the second member has at least one slot that extends in a shape of an arc of a circle with the first axis as a center.

14. The mount according to claim 2, comprising:
a spacer that spaces apart the first member and the second member,
wherein the first member has a first rotational sliding surface closest to the contact section of the second member, and
the spacer is provided at either one of the first rotational sliding surface and the contact section.

15. The mount according to claim 14,
wherein the second member has at least one slot that extends in a shape of an arc of a circle with the first axis as a center.

16. The mount according to claim 14, wherein the spacer extends from one of the first rotational sliding surface and the contact section and has a curved surface facing another one of the first rotational sliding surface and the contact section.

17. The mount according to claim 14, wherein the spacer includes a plurality of spacers between the first member and the second member.

18. The mount according to claim 2,
wherein the second member has at least one slot that extends in a shape of an arc of a circle with the first axis as a center.

19. An endoscope device comprising:
the mount according to claim 1; and
an endoscope configured to image a subject,
wherein the second member includes a pressing section configured to press the endoscope the first axis when the endoscope is connected to the second member.

20. The mount according to claim 1, wherein an inside diameter of the contact section is approximately equal to an outside diameter of the restriction member.

* * * * *